US011300512B2

(12) United States Patent
Moriarty, Jr.

(10) Patent No.: US 11,300,512 B2
(45) Date of Patent: Apr. 12, 2022

(54) DRAWER ORGANIZING SYSTEM

(71) Applicant: Edward C. Moriarty, Jr., Ashland, MA (US)

(72) Inventor: Edward C. Moriarty, Jr., Ashland, MA (US)

(*) Notice: Subject to any disclaimer, the term of this patent is extended or adjusted under 35 U.S.C. 154(b) by 236 days.

(21) Appl. No.: 16/792,972

(22) Filed: Feb. 18, 2020

(65) Prior Publication Data

US 2021/0100362 A1 Apr. 8, 2021

(51) Int. Cl.
| | |
|---|---|
| *A47B 88/975* | (2017.01) |
| *G01N 21/64* | (2006.01) |
| *G06T 7/521* | (2017.01) |
| *G01S 17/89* | (2020.01) |
| *G09F 15/00* | (2006.01) |
| *G09F 23/00* | (2006.01) |
| *G01S 7/483* | (2006.01) |

(52) U.S. Cl.
CPC ....... *G01N 21/6456* (2013.01); *A47B 88/975* (2017.01); *G01S 17/89* (2013.01); *G06T 7/521* (2017.01); *G09F 15/0006* (2013.01); *G09F 23/00* (2013.01); *G01S 7/483* (2013.01); *G06T 2207/10064* (2013.01); *G06T 2207/10068* (2013.01)

(58) Field of Classification Search
CPC .... A47B 88/975; G09F 15/0006; G09F 23/00
USPC .................. 312/348.3, 234–234.5
See application file for complete search history.

(56) References Cited

U.S. PATENT DOCUMENTS

| | | | | |
|---|---|---|---|---|
| 2,306,412 | A | | 12/1942 | Seifert |
| 3,355,231 | A | * | 11/1967 | Kegel ................ A47B 88/994 312/45 |
| 3,700,300 | A | * | 10/1972 | Davis ................ A47B 57/08 312/240 |
| 5,553,710 | A | * | 9/1996 | Takama .............. A47B 88/90 206/561 |
| 5,603,559 | A | | 2/1997 | Yemini |
| 5,738,425 | A | | 4/1998 | Rosenberg |
| 6,733,095 | B1 | | 5/2004 | Rieb |
| 7,163,118 | B2 | * | 1/2007 | Cheng ................ A47B 88/90 220/528 |
| D587,933 | S | * | 3/2009 | Semrau ................ D6/671 |

(Continued)

FOREIGN PATENT DOCUMENTS

WO 9806300 2/1998

*Primary Examiner* — Daniel J Troy
*Assistant Examiner* — Timothy M Ayres
(74) *Attorney, Agent, or Firm* — Kyle A. Fletcher, Esq.

(57) ABSTRACT

The drawer organization system comprises a cabinet and one or more drawers. The one or more drawers are contained within the cabinet. Each of the one or more drawers are organized into a plurality of containment sections. A user organizes the storage of the one or more objects by properly selecting a containment section selected from the plurality of containment sections for each object. The drawer organization system further comprises an index display and a plurality of stickers. The index display is contained within the cabinet. The index display is a display surface on which an index that identifies the selected containment space for each stored object. Each of the plurality of stickers presents the image of an indicia that is attached to a containment space selected from the plurality of containment spaces that relates the selected containment space to the index display.

19 Claims, 7 Drawing Sheets

(56) References Cited

U.S. PATENT DOCUMENTS

| | | | |
|---|---|---|---|
| D712,153 S * | 9/2014 | Lee .................................. D3/319 |
| 8,833,881 B2 | 9/2014 | Manniso | |
| D715,076 S | 10/2014 | Duvigneau | |
| 10,286,542 B2 | 5/2019 | Wolle | |
| 10,314,399 B2 * | 6/2019 | Wolle ..................... A47B 88/90 |
| 2003/0227241 A1 * | 12/2003 | LaBonia, Jr. .......... A47B 88/90 |
| | | | 312/348.3 |
| 2007/0247037 A1 * | 10/2007 | Schenker ............. A47B 88/975 |
| | | | 312/223.6 |
| 2012/0262043 A1 * | 10/2012 | Lechert, Jr. ............ A47B 88/90 |
| | | | 312/348.3 |
| 2018/0344029 A1 * | 12/2018 | Miles .................. A47B 88/975 |

* cited by examiner

DRAWER ORGANIZING SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of cabinets including drawers for cabinets, more specifically, a cabinet further comprising drawers having a means for organizing and sorting the contents in the form of inserts. (A47B88/994)

SUMMARY OF INVENTION

The drawer organization system comprises a cabinet and one or more drawers. The one or more drawers are contained within the cabinet. The drawer organization system is configured for use in organizing a plurality of objects. Each of the one or more drawers are organized into a plurality of containment sections. Each of the plurality of containment sections is a segregated space used for storing one or more objects selected from the plurality of objects. A user organizes the storage of the one or more objects by properly selecting a containment section selected from the plurality of containment sections within which each object selected from the plurality of objects is stored.

The drawer organization system further comprises an index display and a plurality of stickers. The index display is contained within the cabinet. The index display is a display surface on which an index that identifies for any object selected from the plurality of objects the containment space selected from the plurality of containment spaces designated to receive the selected object. Each of the plurality of stickers presents the image of an indicia that is attached to a containment space selected from the plurality of containment spaces that relates the selected containment space to the index display. In the first potential embodiment of the disclosure, the indicia on the plurality of stickers are the letters of an alphabet such that the plurality of objects may be organized alphabetically.

These together with additional objects, features and advantages of the drawer organization system will be readily apparent to those of ordinary skill in the art upon reading the following detailed description of the presently preferred, but nonetheless illustrative, embodiments when taken in conjunction with the accompanying drawings.

In this respect, before explaining the current embodiments of the drawer organization system in detail, it is to be understood that the drawer organization system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the drawer organization system.

It is therefore important that the claims be regarded as including such equivalent construction insofar as they do not depart from the spirit and scope of the drawer organization system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
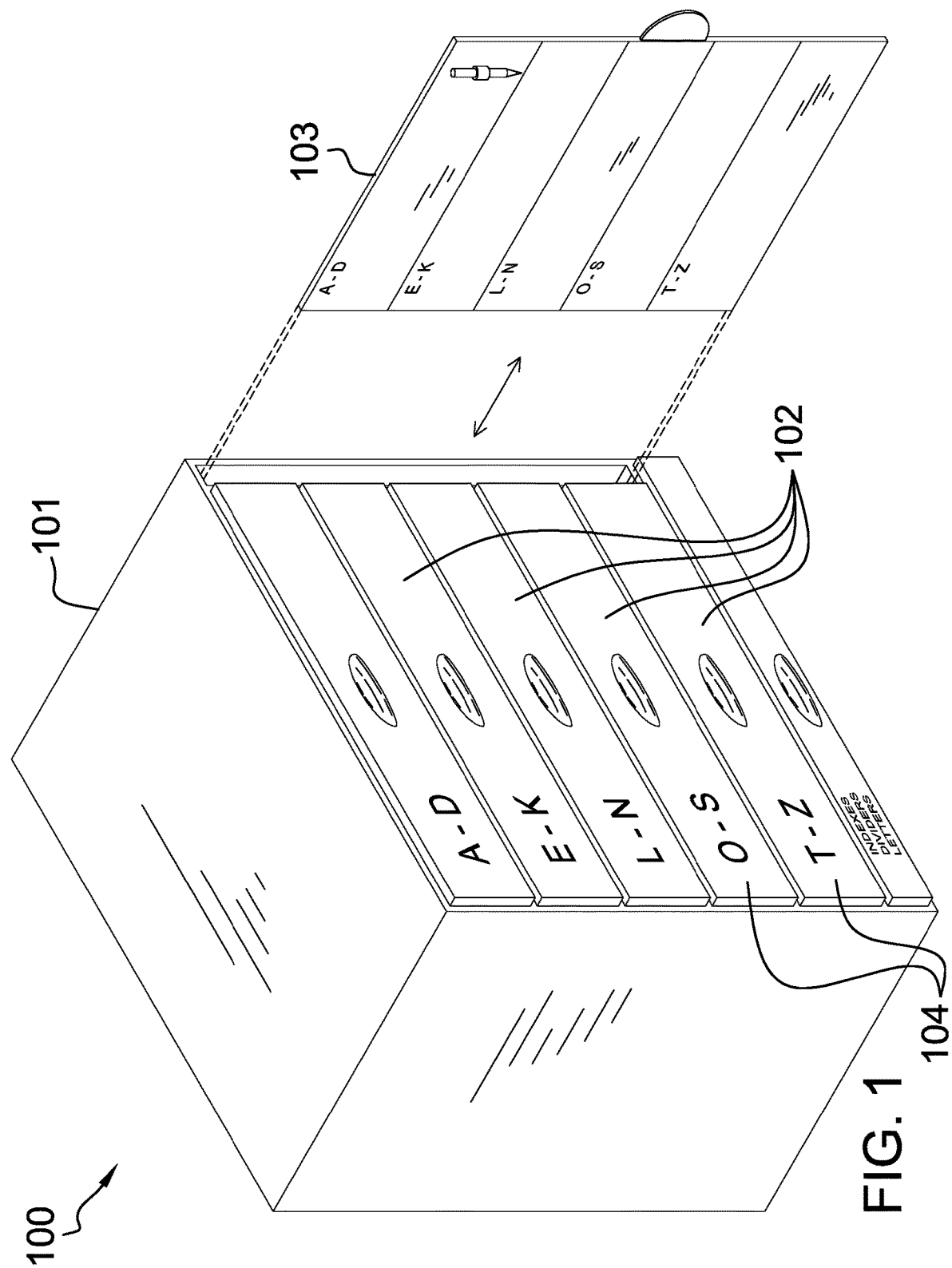
FIG. 1 is a perspective view of an embodiment of the disclosure.
Figure 2:
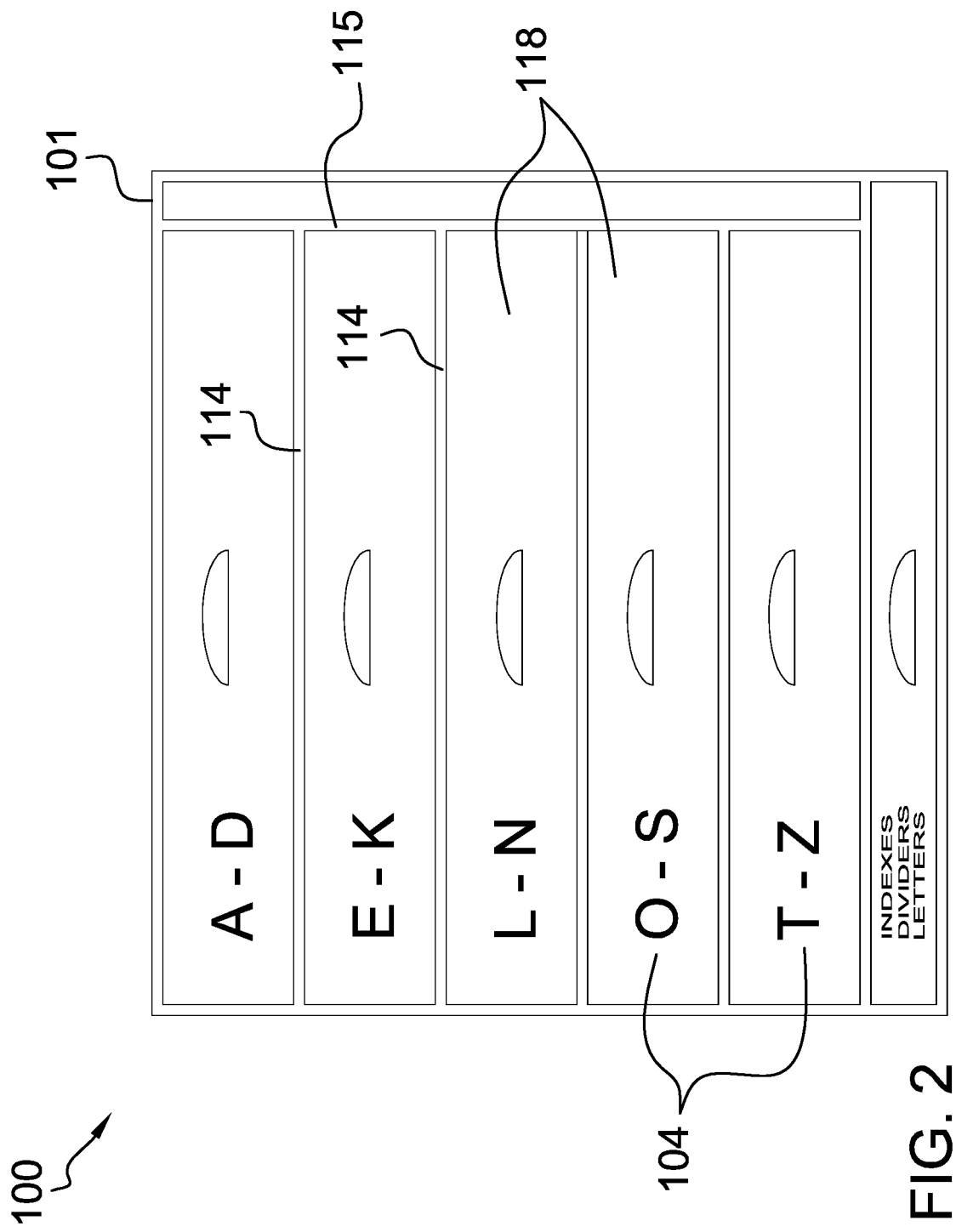
FIG. 2 is a front view of an embodiment of the disclosure.
Figure 3:
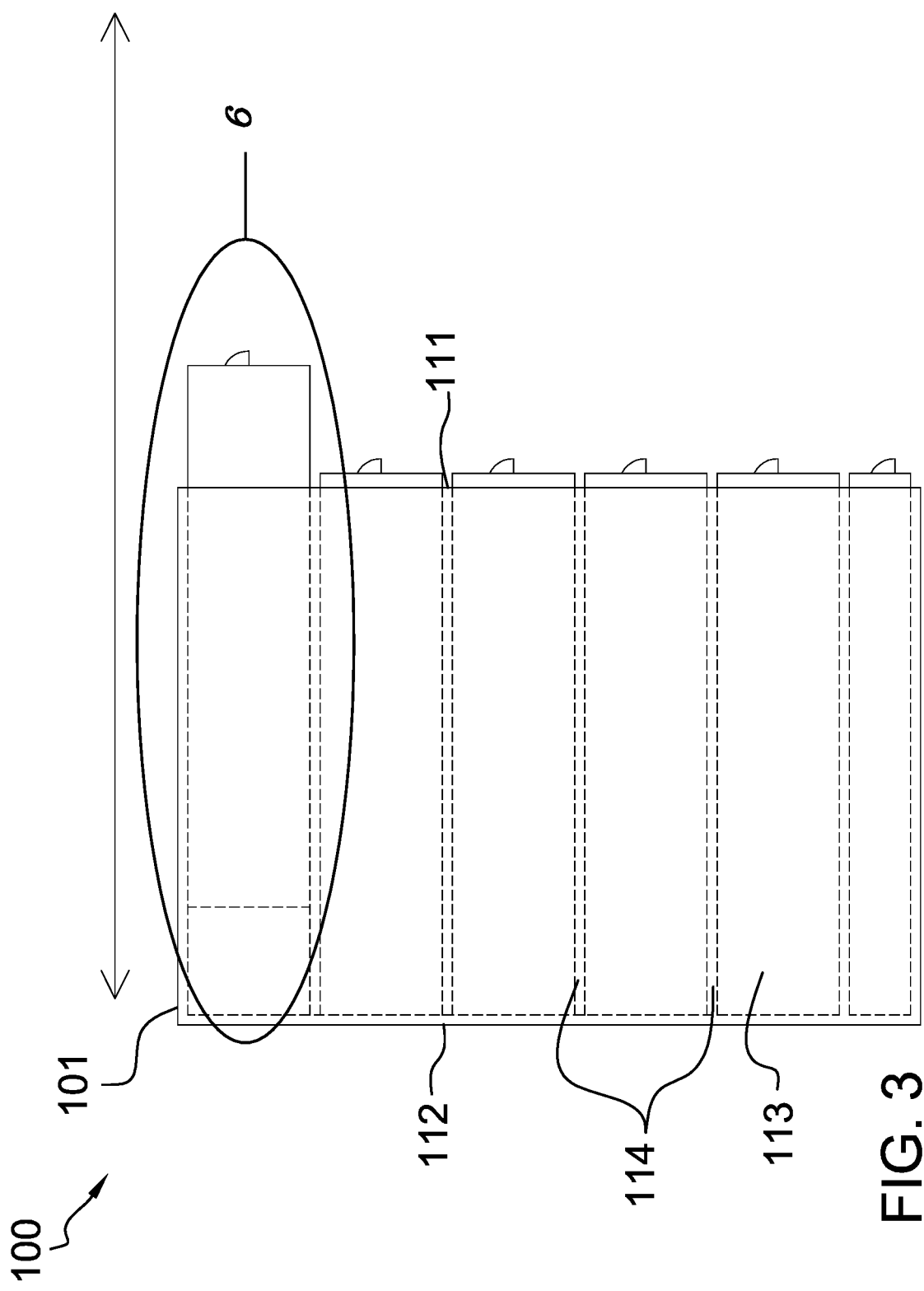
FIG. 3 is a side view of an embodiment of the disclosure.
Figure 4:
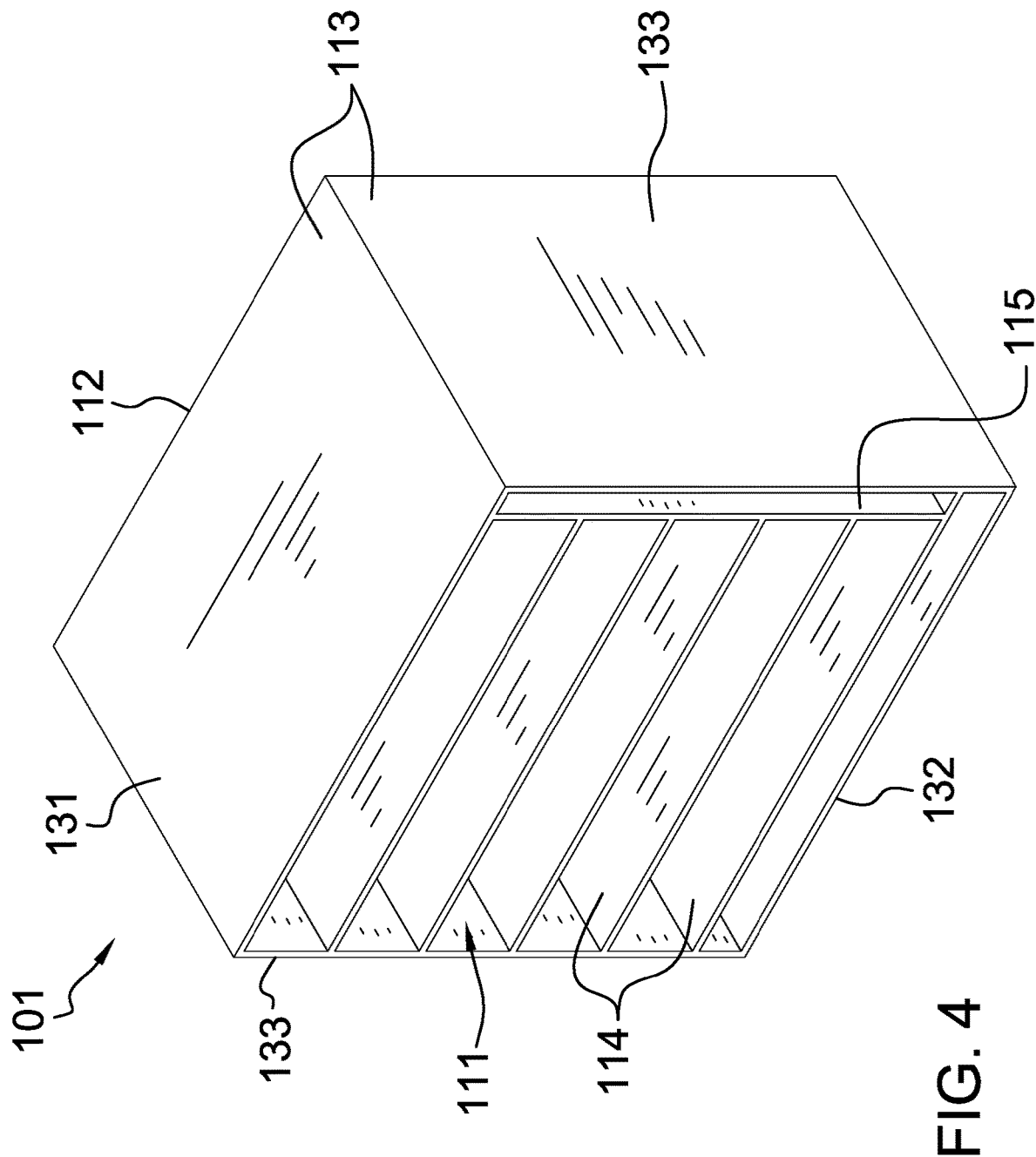
FIG. 4 is a detail view of an embodiment of the disclosure.
Figure 5:
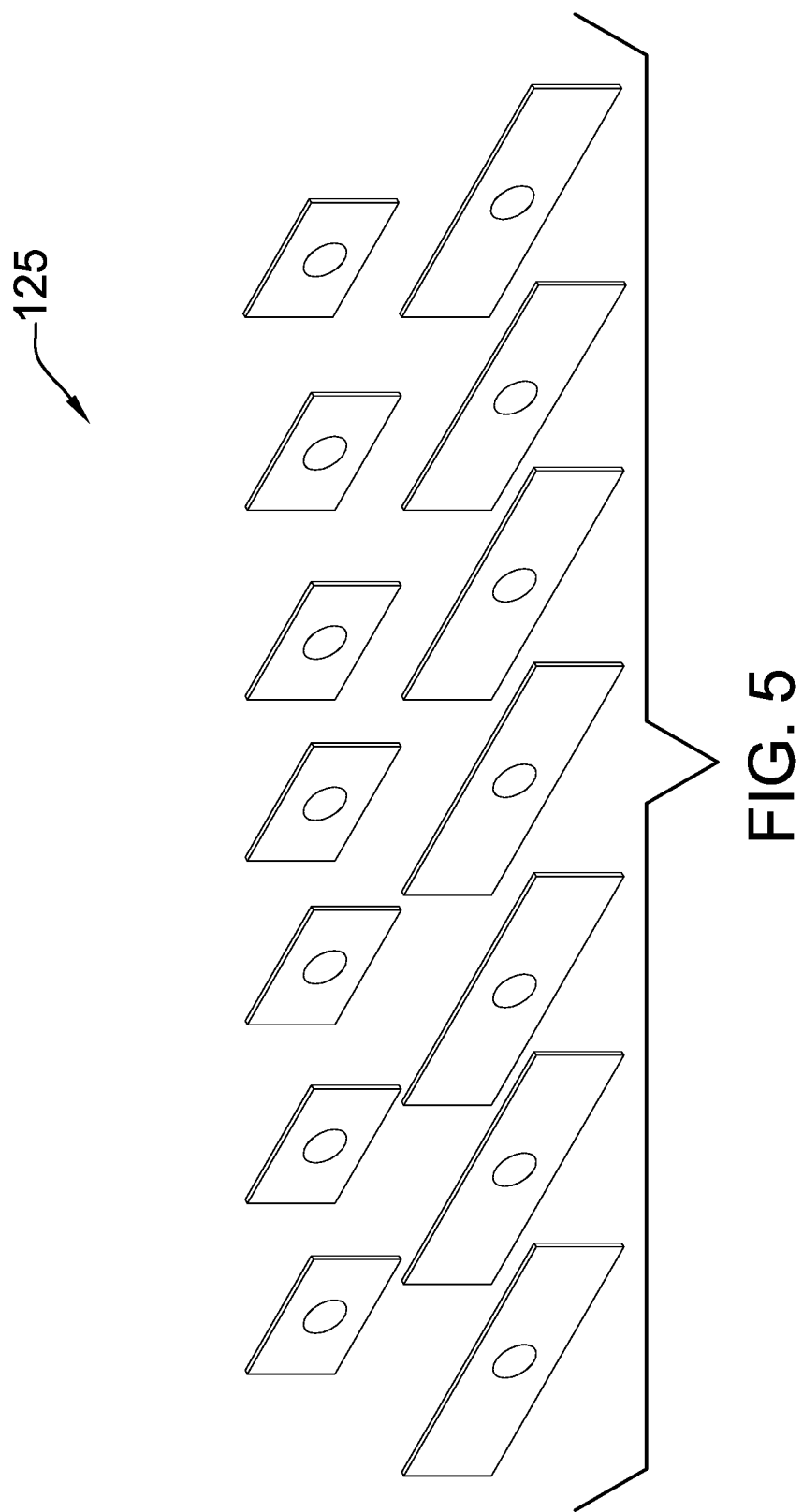
FIG. 5 is a detail view of an embodiment of the disclosure.
Figure 6:
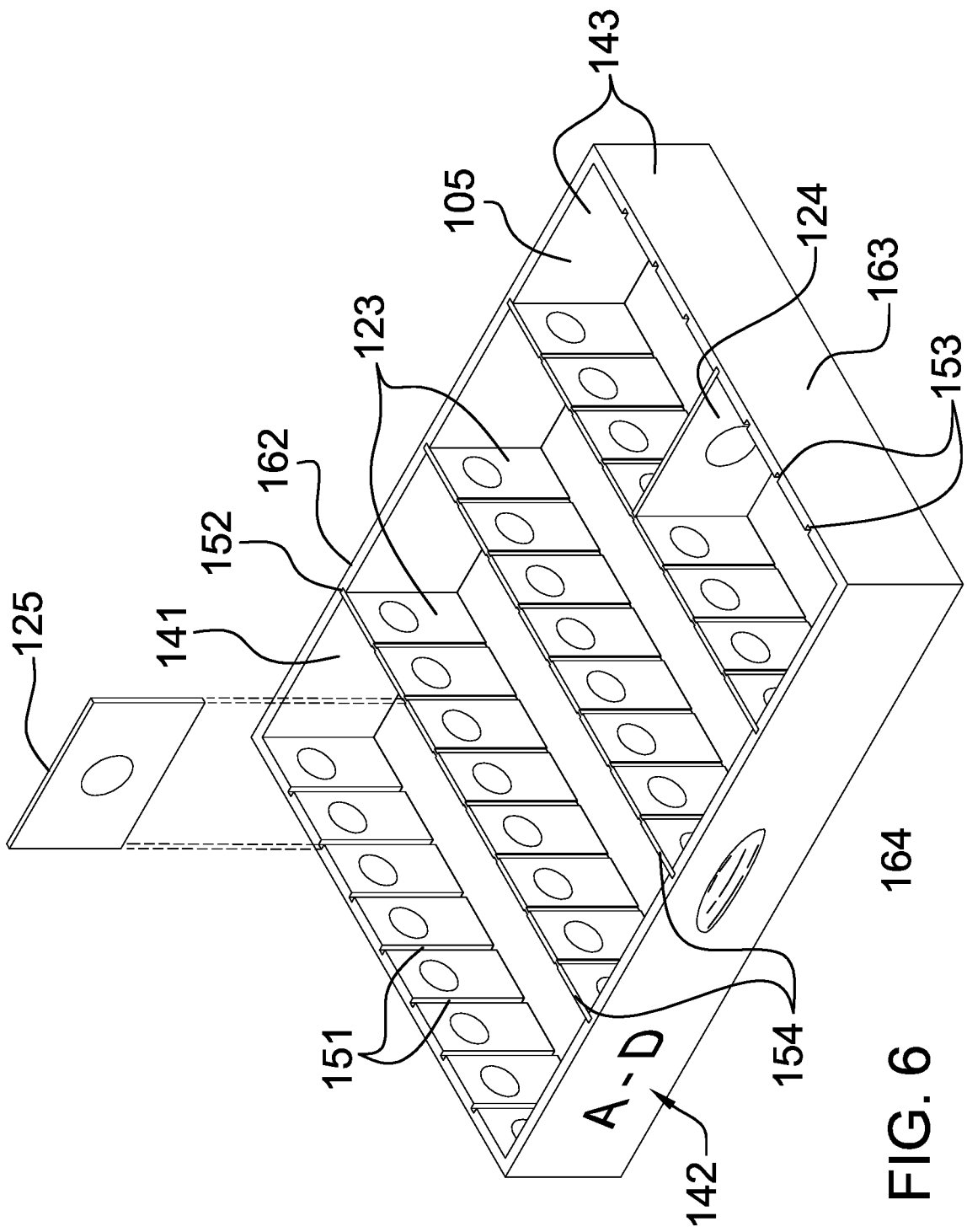
FIG. 6 is an exploded view of an embodiment of the disclosure.
Figure 7:
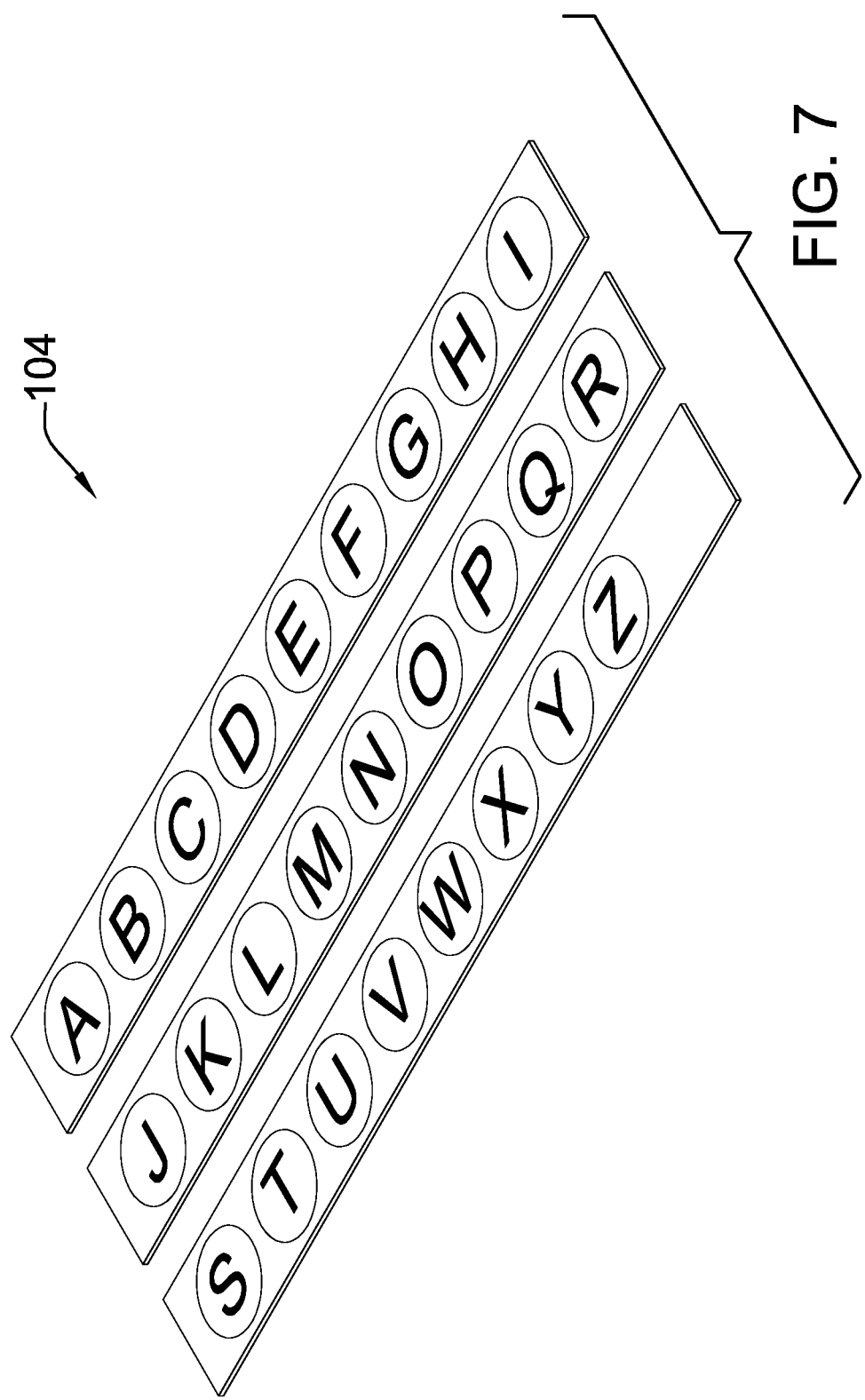
FIG. 7 is a detail view of an embodiment of the disclosure.

Detailed reference will now be made to one or more potential embodiments of the disclosure, which are illustrated in FIGS. 1 through 7.

The drawer organization system 100 (hereinafter invention) comprises a cabinet 101 and one or more drawers 102. The one or more drawers 102 are contained within the cabinet 101. The invention 100 is configured for use in organizing a plurality of objects. Each of the one or more drawers 102 are organized into a plurality of containment sections 105. Each of the plurality of containment sections 105 is a segregated space used for storing one or more objects selected from the plurality of objects. A user organizes the storage of one or more objects by properly selecting a containment section selected from the plurality of containment sections 105 within which each object selected from the plurality of objects is stored.

The invention 100 further comprises an index display 103 and a plurality of stickers 104. The index display 103 is contained within the cabinet 101. The index display 103 is a display surface on which an index that identifies for any object selected from the plurality of objects the containment space selected from the plurality of containment spaces designated to receive the selected object. Each of the plurality of stickers 104 presents the image of an indicia that is attached to a containment space selected from the plurality of containment spaces that relates the selected containment space to the index display 103. In the first potential embodiment of the disclosure, the indicia on the plurality of stickers 104 are the letters of an alphabet such that the plurality of objects may be organized alphabetically.

Each of the plurality of containment sections 105 is a pan shaped structure that is formed within an individual drawer pan 121 selected from the one or more drawers 102. Each of the plurality of containment sections 105 is horizontally bounded by the closed pan face 142 of the associated individual drawer pan 121. The plurality of containment sections 105 are vertically bounded by a structure selected from the group consisting of a transverse divider selected from the one or more transverse dividers 123 and a coronal divider selected from the one or more coronal dividers 124. Each of the plurality of containment sections 105 forms a segregated containment space used to store an object.

The index display 103 is a prism-shaped structure. The index display 103 has a disk shape. The index display 103 removably inserts into the cabinet 101 for storage. The index display 103 forms a surface on which an index is displayed. The index displayed by the index display 103 relates the location of each object selected from the plurality of objects stored in the invention 100 to a containment structure selected from the plurality of containment sections 105. In the first potential embodiment of the disclosure, the index display 103 is formed from a whiteboard.

Each of the plurality of stickers 104 is a label. Each of the plurality of stickers 104 attaches to an individual drawer pan 121 selected from the one or more drawers 102. Each of the plurality of stickers 104 is a label. The sentiment displayed by each sticker selected from the plurality of stickers 104 links the index information provided by the index display 103 to a structure selected from the group consisting of: a) the individual drawer pan 121; and, b) a containment section selected from the plurality of containment sections 105. The position of each sticker selected from the plurality of stickers 104 is such that the selected sticker properly labels the selected structure to match the index display 103. Each of the plurality of stickers 104 provides visual identification of a location identified by the index display 103.

The cabinet 101 is a prism-shaped structure. The cabinet 101 is a hollow structure. The cabinet 101 has a pan shape. The cabinet 101 contains the one or more drawers 102 such that each individual drawer pan 121 slides into and out of the cabinet 101. The cabinet 101 contains the index display 103. The cabinet 101 forms a portion of the exterior surface of the invention 100.

The cabinet 101 further comprises a cabinet 101 open face 111, a cabinet 101 closed face 112, and a plurality of cabinet 101 lateral faces 113.

The cabinet 101 open face 111 is the open face of the pan structure of the cabinet 101. Each of the one or more drawers 102 inserts into the cabinet 101 and is removed from the cabinet 101 through the cabinet 101 open face 111. The cabinet 101 open face 111 forms the anterior vertical surface of the prism structure of the cabinet 101.

The cabinet 101 closed face 112 is the closed face of the pan structure of the cabinet 101. The cabinet 101 closed face 112 is a disk-shaped plate structure. The cabinet 101 closed face 112 forms the posterior vertical surface of the prism structure of the cabinet 101. The cabinet 101 closed face 112 is the face of the prism structure of the cabinet 101 that is distal from the cabinet 101 open face 111.

Each of the plurality of cabinet 101 lateral faces 113 forms a lateral face of the prism structure of the cabinet 101. Each of the plurality of cabinet 101 lateral faces 113 forms a portion of the exterior surface of the cabinet 101 that is formed in the regions between the cabinet 101 open face 111 and the cabinet 101 closed face 112. Each of the plurality of cabinet 101 lateral faces 113 is a disk-shaped plate structure.

The plurality of cabinet 101 lateral faces 113 further comprises a superior cabinet 101 face 131, an inferior cabinet 101 face 132, and a plurality of vertical faces 133.

The superior cabinet 101 face 131 is a lateral face selected from the plurality of cabinet 101 lateral faces 113. The superior cabinet 101 face 131 forms the superior surface of the invention 100. The inferior cabinet 101 face 132 is a lateral face selected from the plurality of cabinet 101 lateral faces 113. The inferior cabinet 101 face 132 forms the inferior surface of the invention 100. The inferior cabinet 101 face 132 is the face of the prism structure of the cabinet 101 that is distal from the superior cabinet 101 face 131. The inferior cabinet 101 face 132 rests on a supporting surface. Each of the plurality of vertical faces 133 forms a vertically oriented boundary of the cabinet 101. Each of the plurality of vertical faces 133 attaches the superior cabinet 101 face 131 to the inferior cabinet 101 face 132.

The cabinet 101 further comprises a plurality of drawer shelves 114 and an index plate 115.

The index plate 115 is a vertically oriented disk-shaped structure installed in the interior space of the cabinet 101. The index plate 115 segregates the interior hollow space of the pan structure of the cabinet 101 into two containment spaces. The first containment space formed by the index plate 115 is sized and configured to receive the one or more drawers 102 for storage. The second containment space formed by the index plate 115 is sized and configured to receive the index display 103 for storage.

The first containment space is bounded by the superior cabinet 101 face 131, the inferior cabinet 101 face 132, a congruent end of the disk structure of the index plate 115, a lateral face selected from the plurality of vertical faces 133, the cabinet 101 open face 111, and the cabinet 101 closed face 112. The second containment space is bounded by the superior cabinet 101 face 131, the inferior cabinet 101 face 132, the congruent end of the disk structure of the index plate 115 opposite to the first containment space, the lateral face selected from the plurality of vertical faces 133 opposite to the first containment space, the cabinet 101 open face 111, and the cabinet 101 closed face 112.

Each of the plurality of drawer shelves 114 is a horizontally oriented disk-shaped structure installed in the interior space of the cabinet 101. More specifically, each of the plurality of drawer shelves 114 form horizontally oriented platforms within the first containment space of the cabinet 101. Each of the plurality of drawer shelves 114 elevates and supports an individual drawer pan 121 selected from the one or more drawers 102 above the superior cabinet 101 face 131. The lateral faces of each of the plurality of drawer shelves 114 attaches to the congruent end of the disk structure of the index plate 115 opposite to the second containment space, the lateral face selected from the plurality of vertical faces 133, and the cabinet 101 closed face 112.

Each of the one or more drawers 102 is a prism-shaped structure. Each of the one or more drawers 102 is a hollow structure. Each of the one or more drawers 102 has a pan shape. Each of the one or more drawers 102 is organized into a plurality of containment sections 105. Each containment structure selected from the plurality of containment sections 105 is a segregated space that stores an object selected from a plurality of objects space separately from the objects remaining in the plurality of objects. Each containment structure selected from the one or more drawers 102 slides into the cabinet 101 for storage. Each individual drawer pan 121 selected from the one or more drawers 102 slides out of the cabinet 101 such that each of the one or more drawers 102 is accessible from the exterior of the cabinet 101. The one or more drawers 102 comprises a collection of individual drawer pans 121.

Each individual drawer pan 121 selected from the one or more drawers 102 is a prism-shaped structure. Each individual drawer pan 121 is a hollow structure. Each individual drawer pan 121 has a pan shape. Each individual drawer pan 121 is organized into the plurality of containment sections 105. Each individual drawer pan 121 inserts into the cabinet 101 such that each individual drawer pan 121 sits on the superior of a drawer shelf selected from the plurality of drawer shelves 114. The hollow interior space of the individual drawer pan 121 contains one or more objects selected from a plurality of objects.

Each individual drawer pan 121 further comprises an open pan face 141, a closed pan face 142, and a plurality of pan lateral faces 143.

The open pan face 141 is the open face of the pan structure of the individual drawer pan 121. The open pan face 141 provides access into the hollow interior of the pan structure of the individual drawer pan 121. The open pan face 141 forms the superior face of the individual drawer pan 121 when the individual drawer pan 121 installs normally in the cabinet 101. The closed pan face 142 is the closed face of the pan structure of the individual drawer pan 121. The closed pan face 142 forms the inferior face of the individual drawer pan 121 when the individual drawer pan 121 installs normally in the cabinet 101. The closed pan face 142 rests directly on a drawer shelf selected from the plurality of drawer shelves 114 of the cabinet 101.

Each of the plurality of pan lateral faces 143 forms a vertically oriented boundary that encloses the hollow interior of the pan structure of the individual drawer pan 121. The plurality of pan lateral faces 143 forms the containment structure of the individual drawer pan 121 between the open pan face 141 and the closed pan face 142. A subset of the plurality of alignment slots 122 are formed on the interior faces of each of the plurality of pan lateral faces 143.

The plurality of pan lateral faces 143 further comprises a first pan lateral face 161, a second pan lateral face 162, a third pan lateral face 163, and a fourth pan lateral face 164.

The first pan lateral face 161 is a disk-shaped plate structure that forms a portion of the lateral face of the pan structure of the individual drawer pan 121. The congruent ends of the disk structure of the first pan lateral face 161 run parallel to the transverse direction of the cabinet 101.

The second pan lateral face 162 is a disk-shaped plate structure that forms a portion of the lateral face of the pan structure of the individual drawer pan 121. The congruent ends of the disk structure of the second pan lateral face 162 runs parallel to the coronal direction of the cabinet 101.

The third pan lateral face 163 is a disk-shaped plate structure that forms a portion of the lateral face of the pan structure of the individual drawer pan 121. The congruent ends of the disk structure of the third pan lateral face 163 runs parallel to the transverse direction of the cabinet 101. The third pan lateral face 163 is the face of the pan structure of the individual drawer pan 121 that is distal from the first pan lateral face 161.

The fourth pan lateral face 164 is a disk-shaped plate structure that forms a portion of the lateral face of the pan structure of the individual drawer pan 121. The congruent ends of the disk structure of the fourth pan lateral face 164 runs parallel to the coronal direction of the cabinet 101. The fourth pan lateral face 164 is the face of the pan structure of the individual drawer pan 121 that is distal from the second pan lateral face 162.

Each individual drawer pan 121 comprises a plurality of alignment slots 122, one or more transverse dividers 123, one or more coronal dividers 124, and a plurality of enclosing plates 125.

Each of the plurality of alignment slots 122 is a slot that is formed on the interior congruent end of the disk structure of a lateral face of a structure selected from the group consisting of: a) an interior vertical surface of the prism structure of the individual drawer pan 121; b) a lateral face of the disk structure of a transverse divider selected from the one or more transverse dividers 123; and, c) a lateral face of the disk structure of a coronal divider selected from the one or more coronal dividers 124. Each of the plurality of alignment slots 122 forms a prism-shaped structure. The major axis of each of the plurality of alignment slots 122 is parallel to the sagittal direction of the cabinet 101 when the individual drawer pan 121 is properly installed in the cabinet 101.

Each of the one or more transverse dividers 123 is a disk-shaped plate structure. Each of the one or more transverse dividers 123 forms a boundary within the individual drawer pan 121 that runs parallel to the transverse direction of the cabinet 101 when the individual drawer pan 121 installs normally within the cabinet 101. The boundary formed by each of the one or more transverse dividers 123 forms a vertical containment boundary of one or more containment sections selected from the plurality of containment sections 105 contained in the individual drawer pan 121. Each of the one or more transverse dividers 123 further comprises a subset of alignment slots selected from the plurality of alignment slots 122. Each of the one or more transverse dividers 123 installs into a first alignment slot selected from the plurality of alignment slots 122 while simultaneously inserting into a second alignment slot selected from the plurality of alignment slots 122.

Each of the one or more coronal dividers 124 is a disk-shaped plate structure. Each of the one or more coronal dividers 124 forms a boundary within the individual drawer pan 121 that runs parallel to the coronal direction of the cabinet 101 when the individual drawer pan 121 installs normally within the cabinet 101. The boundary formed by each of the one or more coronal dividers 124 forms a vertical containment boundary of one or more containment sections selected from the plurality of containment sections 105 contained in the individual drawer pan 121. Each of the one or more coronal dividers 124 further comprises a subset of alignment slots selected from the plurality of alignment slots 122. Each of the one or more coronal dividers 124 installs into a first alignment slot selected from the plurality of alignment slots 122 while simultaneously inserting into a second alignment slot selected from the plurality of alignment slots 122.

The plurality of enclosing plates 125 is a disk-shaped plate structure. The plurality of enclosing plates 125 forms a boundary within the individual drawer pan 121. The boundary formed by each of the plurality of enclosing plates 125 forms a vertical containment boundary of one or more containment sections selected from the plurality of containment sections 105 contained in the individual drawer pan 121. Each of the plurality of enclosing plates 125 installs into a first alignment slot selected from the plurality of alignment slots 122 while simultaneously inserting into a second alignment slot selected from the plurality of alignment slots 122.

The further subset of alignment slots selected from the plurality of alignment slots 122 comprises a first set of alignment slots 151, a second set of alignment slots 152, a third set of alignment slots 153, and a fourth set of alignment slots 154.

The first set of alignment slots 151 is a subset of alignment slots selected from the plurality of alignment slots 122 formed in the interior face of the first pan lateral face 161. The second set of alignment slots 152 is a subset of alignment slots selected from the plurality of alignment slots 122 formed in the interior face of the second pan lateral face 162. The third set of alignment slots 153 is a subset of alignment slots selected from the plurality of alignment slots 122 formed in the interior face of the third pan lateral face 163. Each of the third set of alignment slots 153 aligns in the coronal direction with an alignment slot selected from the first set of alignment slots 151. The fourth set of alignment slots 154 is a subset of alignment slots selected from the plurality of alignment slots 122 formed in the interior face of the fourth pan lateral face 164. Each of the fourth set of alignment slots 154 aligns in the coronal direction with an alignment slot selected from the second set of alignment slots 152.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Alphabet: As used in this disclosure, an alphabet refers to a plurality of images used in a written language. Each image selected from the plurality of images is called a letter. Each letter is an indicia that is placed in a predetermined order, referred to as a spelling, with one or more additional letters selected from the alphabet to generate the sentiment of a word of the language. Each letter further imparts phonetic information. The indicia of each letter, both alone and in combination with other letters, provides a sentiment indicating the pronunciation of the word. The English alphabet, also referred to as the Carolingian alphabet, is a 26 letter alphabet derived from the Latin alphabet. The English alphabet comprises the letters: A, B, C, D, E, F, G, H, I, J, K, L, M, N, O, P, Q, R, S, T U, V, W, X, Y, and Z. In the English language, a collection of objects that are alphabetically organized are organized in the order presented above.

Anterior: As used in this disclosure, anterior is a term that is used to refer to the front side or direction of a structure. When comparing two objects, the anterior object is the object that is closer to the front of the structure.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Coronal Direction: As used in this disclosure, the coronal direction is a direction that runs between the lateral surfaces of an object and that is perpendicular to the sagittal direction and the transverse direction.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Distal: As used in this disclosure, distal refers to a directional sense or location of an object. Specifically, distal refers to a first object, or a side of a first object, that is distal from the medial axis, or more proximal to the side of the object, relative to a second object, or side of a second object.

Exterior: As used in this disclosure, the exterior is used as a relational term that implies that an object is not contained within the boundary of a structure or a space.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Label: As used in this disclosure, a label is an image of an indicia that attaches to an object. The indicia of the label provides a sentiment about the object to which the label attaches.

Lateral: As used in this disclosure, the term lateral refers to an axis of an object that is perpendicular in the horizontal plane to the primary sense of direction of the object. Lateral movement is always perpendicular to the anterior-posterior axis. Lateral sides form the boundary of a coronal plane.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to the longest edge of a rectangular structure.

Medial: As used in this disclosure, medial refers to a directional sense or location of an object. Specifically, medial refers to a first object or a side of a first object that is closer to the medial axis or more distal from the side of the object relative to a second object or side of a second object.

Medial Axis: As used in this disclosure, the medial axis is the center line of an as the line is drawn from the superior surface to the inferior surface. When two objects are compared relative to the medial axis, the object closer to the medial axis is referred to as the medial object and the object distal from the medial axis is referred to as the lateral object.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Perimeter: As used in this disclosure, a perimeter is one or more curved or straight lines that bounds an enclosed area on a plane or surface. The perimeter of a circle is commonly referred to as a circumference.

Plate: As used in this disclosure, a plate is a smooth, flat and semi-rigid or rigid structure that has at least one dimension that: a) is of uniform thickness; and b) that appears thin relative to the other dimensions of the object. Plates are often disks. The face of the plate is a surface of the plate selected from the group consisting of: a) the surface of the plate with the greatest surface area; b) the surface of the plate that is distal from the surface of the plate with the greatest surface area. The edges of the plate comprises the surfaces of the plate that would not be considered faces as defined above. As defined in this disclosure, plates may be made of any material, but are commonly made of metal, plastic, and wood. When made of wood, a plate is often referred to as a board.

Posterior: As used in this disclosure, posterior is a term that is used to refer to the side of an object that is distal or in the opposite direction of the anterior side. When comparing two items, the posterior item is the item that is distal from the anterior of the object.

Primary Sense of Direction: As used in this disclosure, the primary sense of direction of an object refers to a vector that: 1) passes through the center of the object; and, 2) is parallel to the direction of travel when the anterior surface(s) of the object are leading the object into the direction of travel. This definition intends to align with what people would normally call the forward direction of an object.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Sagittal Direction: As used in this disclosure, the sagittal direction runs from the superior surface to the inferior surface of an object and is perpendicular to the coronal direction and the transverse direction.

Shelf: As used in this disclosure, a shelf is a horizontal surface that supports one or more objects at an elevated position.

Slot: As used in this disclosure, a slot is a prism-shaped groove or aperture that is formed in an object.

Superior: As used in this disclosure, the term superior refers to a directional reference that is parallel to and in the opposite direction of the force of gravity when an object is positioned or used normally.

Transverse Direction: As used in this disclosure, the transverse direction runs from the anterior surface to the posterior surface of an object and is perpendicular to the coronal direction and the sagittal direction.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Whiteboard: As used in this disclosure, a whiteboard is a surface that is designed to receive non-permanent markings that can be used for communication or recordation purposes. This definition is explicitly intended to include chalkboards. Whiteboards are also commonly referred to as dry erase boards.

The following definition was used in this disclosure:

The following definitions and directional references were used in this disclosure:

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A drawer organization system comprising
   comprises a cabinet and one or more drawers;
   wherein the one or more drawers are contained within the cabinet;
   wherein the drawer organization system is configured for use in organizing a plurality of objects;
   wherein each of the one or more drawers are organized into a plurality of containment sections;
   wherein each of the plurality of containment sections is a segregated space used for storage;
   wherein the storage of the one or more objects is organized by properly selecting a containment section selected from the plurality of containment sections for storage of an item;
   wherein the drawer organization system further comprises an index display and a plurality of stickers;
   wherein the cabinet further comprises a plurality of drawer shelves and an index plate;
   wherein the index plate is installed in an interior space of the cabinet;
   wherein the index plate segregates an interior hollow space of the pan structure of the cabinet into a first containment space and a second containment space;
   wherein the first containment space formed by the index plate is sized and configured to receive the one or more drawers for storage;
   wherein the second containment space formed by the index plate is sized and configured to receive the index display for storage;
   wherein the first containment space is bounded by the superior cabinet face, the inferior cabinet face, a congruent end of the disk structure of the index plate, a lateral face selected from the plurality of vertical faces, the cabinet open face, and the cabinet closed face;
   wherein the second containment space is bounded by the superior cabinet face, the inferior cabinet face, the congruent end of the disk structure of the index plate opposite to the first containment space, the lateral face selected from the plurality of vertical faces opposite to the first containment space, the cabinet open face, and the cabinet closed face.

2. The drawer organization system according to claim 1
   wherein the index display is contained within the cabinet;
   wherein the index display is a display surface on which an index that identifies the location of any object stored in a containment space selected from the plurality of containment spaces;
   wherein each of the plurality of stickers presents an image of an indicia that is attached to a containment space selected from the plurality of containment spaces that relates the selected containment space to the index display.

3. The drawer organization system according to claim 2 wherein the indicia on the plurality of stickers are the letters of an alphabet such that storage is organized alphabetically.

4. The drawer organization system according to claim 3
   wherein the one or more drawers comprises a collection of individual drawer pans;
   wherein each individual drawer pan selected from the one or more drawers slides out of the cabinet such that each of the one or more drawers is accessible from the exterior of the cabinet.

5. The drawer organization system according to claim 4
   wherein each of the plurality of containment sections is a pan shaped structure that is formed within an individual drawer pan selected from the one or more drawers;
   wherein each of the plurality of containment sections is horizontally bounded by the closed pan face of the associated individual drawer pan.

6. The drawer organization system according to claim 5
   wherein the index display removably inserts into the cabinet for storage;
   wherein the index display forms a surface on which an index is displayed;
   wherein the index displayed by the index display relates the location of each object selected from the plurality of objects stored in the drawer organization system to a containment structure selected from the plurality of containment sections.

7. The drawer organization system according to claim 6
   wherein the index display is a prism-shaped structure;
   wherein the index display has a disk shape.

8. The drawer organization system according to claim 7
   wherein each of the plurality of stickers is a label that displays an image that presents an indicia that indicates a sentiment;
   wherein each of the plurality of stickers attaches to an individual drawer pan selected from the one or more drawers;
   wherein the sentiment displayed by each sticker selected from the plurality of stickers links the index information provided by the index display to a structure selected from the group consisting of: a) the individual drawer pan; and, b) a containment section selected from the plurality of containment sections;
   wherein the position of each sticker selected from the plurality of stickers is such that the selected sticker properly labels the selected structure to match the index display;
   wherein each of the plurality of stickers provides visual identification of a location identified by the index display.

9. The drawer organization system according to claim 8
   wherein the cabinet is a prism-shaped structure;
   wherein the cabinet is a hollow structure;
   wherein the cabinet has a pan shape;
   wherein the cabinet contains the one or more drawers such that each individual drawer pan slides into and out of the cabinet.

10. The drawer organization system according to claim 9
wherein each of the one or more drawers is a prism-shaped structure;
wherein each of the one or more drawers is a hollow structure;
wherein each of the one or more drawers has a pan shape;
wherein each of the one or more drawers is organized into a plurality of containment sections;
wherein each containment structure selected from the plurality of containment sections is a segregated space that stores an object selected from a plurality of objects space separately from the objects remaining in the plurality of objects;
wherein each containment structure selected from the one or more drawers slides into the cabinet for storage.

11. The drawer organization system according to claim 10
wherein the cabinet further comprises a cabinet open face, a cabinet closed face, and a plurality of cabinet lateral faces;
wherein the cabinet open face is the open face of the pan structure of the cabinet;
wherein each of the one or more drawers inserts into the cabinet and is removed from the cabinet through the cabinet open face;
wherein the cabinet open face forms the anterior vertical surface of the prism structure of the cabinet;
wherein the cabinet closed face is the closed face of the pan structure of the cabinet;
wherein the cabinet closed face is a disk-shaped plate structure;
wherein the cabinet closed face forms the posterior vertical surface of the prism structure of the cabinet;
wherein the cabinet closed face is the face of the prism structure of the cabinet that is distal from the cabinet open face;
wherein each of the plurality of cabinet lateral faces forms a lateral face of the prism structure of the cabinet;
wherein each of the plurality of cabinet lateral faces forms a portion of the exterior surface of the cabinet that is formed in the regions between the cabinet open face and the cabinet closed face;
wherein each of the plurality of cabinet lateral faces is a disk-shaped plate structure.

12. The drawer organization system according to claim 11
wherein the plurality of cabinet lateral faces further comprises a superior cabinet face, an inferior cabinet face, and a plurality of vertical faces;
wherein the superior cabinet face is a lateral face selected from the plurality of cabinet lateral faces;
wherein the superior cabinet face forms the superior surface of the drawer organization system;
wherein the inferior cabinet face is a lateral face selected from the plurality of cabinet lateral faces;
wherein the inferior cabinet face forms the inferior surface of the drawer organization system;
wherein the inferior cabinet face is the face of the prism structure of the cabinet that is distal from the superior cabinet face;
wherein the inferior cabinet face rests on a supporting surface;
wherein each of the plurality of vertical faces forms a vertically oriented boundary of the cabinet;
wherein each of the plurality of vertical faces attaches the superior cabinet face to the inferior cabinet face.

13. The drawer organization system according to claim 12
wherein each of the plurality of drawer shelves is a horizontally oriented disk-shaped structure installed in the interior space of the cabinet;
wherein each of the plurality of drawer shelves supports an individual drawer pan selected from the one or more drawers;
wherein each of the plurality of drawer shelves form horizontally oriented platforms within the first containment space of the cabinet;
wherein each of the plurality of drawer shelves elevates and supports an individual drawer pan selected from the one or more drawers above the superior cabinet face;
wherein the lateral faces of each of the plurality of drawer shelves attaches to the congruent end of the disk structure of the index plate opposite to the second containment space, the lateral face selected from the plurality of vertical faces, and the cabinet closed face.

14. The drawer organization system according to claim 13
wherein each individual drawer pan selected from the one or more drawers is a prism-shaped structure;
wherein each individual drawer pan is a hollow structure;
wherein each individual drawer pan has a pan shape;
wherein each individual drawer pan is organized into the plurality of containment sections;
wherein each individual drawer pan inserts into the cabinet such that each individual drawer pan sits on the superior of a drawer shelf selected from the plurality of drawer shelves.

15. The drawer organization system according to claim 14
wherein each individual drawer pan further comprises an open pan face, a closed pan face, and a plurality of pan lateral faces;
wherein the open pan face is the open face of the pan structure of the individual drawer pan;
wherein the open pan face provides access into the hollow interior of the pan structure of the individual drawer pan;
wherein the open pan face forms the superior face of the individual drawer pan when the individual drawer pan installs normally in the cabinet;
wherein the closed pan face is the closed face of the pan structure of the individual drawer pan;
wherein the closed pan face forms the inferior face of the individual drawer pan when the individual drawer pan installs normally in the cabinet;
wherein the closed pan face rests directly on a drawer shelf selected from the plurality of drawer shelves of the cabinet;
wherein each of the plurality of pan lateral faces forms a vertically oriented boundary that encloses the hollow interior of the pan structure of the individual drawer pan;
wherein the plurality of pan lateral faces forms the containment structure of the individual drawer pan between the open pan face and the closed pan face;
wherein the plurality of pan lateral faces further comprises a first pan lateral face, a second pan lateral face, a third pan lateral face, and a fourth pan lateral face;
wherein the first pan lateral face is a disk-shaped plate structure that forms a portion of the lateral face of the pan structure of the individual drawer pan;
wherein the congruent ends of the disk structure of the first pan lateral face run parallel to the transverse direction of the cabinet;

wherein the second pan lateral face is a disk-shaped plate structure that forms a portion of the lateral face of the pan structure of the individual drawer pan;

wherein the congruent ends of the disk structure of the second pan lateral face runs parallel to the coronal direction of the cabinet;

wherein the third pan lateral face is a disk-shaped plate structure that forms a portion of the lateral face of the pan structure of the individual drawer pan;

wherein the congruent ends of the disk structure of the third pan lateral face runs parallel to the transverse direction of the cabinet;

wherein the third pan lateral face is the face of the pan structure of the individual drawer pan that is distal from the first pan lateral face;

wherein the fourth pan lateral face is a disk-shaped plate structure that forms a portion of the lateral face of the pan structure of the individual drawer pan;

wherein the congruent ends of the disk structure of the fourth pan lateral face runs parallel to the coronal direction of the cabinet;

wherein the fourth pan lateral face is the face of the pan structure of the individual drawer pan that is distal from the second pan lateral face.

16. The drawer organization system according to claim 15 wherein each individual drawer pan further comprises a plurality of alignment slots, one or more transverse dividers, one or more coronal dividers, and a plurality of enclosing plates;

wherein a subset of the plurality of alignment slots are formed on the interior faces of each of the plurality of pan lateral faces;

wherein each of the plurality of alignment slots is a slot that is formed on the interior congruent end of the disk structure of a lateral face of a structure selected from the group consisting of: a) an interior vertical surface of the prism structure of the individual drawer pan; b) a lateral face of the disk structure of a transverse divider selected from the one or more transverse dividers; and, c) a lateral face of the disk structure of a coronal divider selected from the one or more coronal dividers;

wherein the plurality of containment sections are vertically bounded by a structure selected from the group consisting of a transverse divider selected from the one or more transverse dividers and a coronal divider selected from the one or more coronal dividers.

17. The drawer organization system according to claim 16 wherein each of the plurality of alignment slots forms a prism-shaped structure;

wherein the major axis of each of the plurality of alignment slots is parallel to the sagittal direction of the cabinet when the individual drawer pan is properly installed in the cabinet.

18. The drawer organization system according to claim 17 wherein each of the one or more transverse dividers is a disk-shaped plate structure;

wherein each of the one or more transverse dividers forms a boundary within the individual drawer pan that runs parallel to the transverse direction of the cabinet when the individual drawer pan installs normally within the cabinet;

wherein the boundary formed by each of the one or more transverse dividers forms a vertical containment boundary of one or more containment sections selected from the plurality of containment sections contained in the individual drawer pan;

wherein each of the one or more transverse dividers further comprises a fifth set of alignment slots selected from the plurality of alignment slots;

wherein each of the one or more transverse dividers installs into a first alignment slot selected from the plurality of alignment slots while simultaneously inserting into a second alignment slot selected from the plurality of alignment slots;

wherein each of the one or more coronal dividers is a disk-shaped plate structure;

wherein each of the one or more coronal dividers forms a boundary within the individual drawer pan that runs parallel to the coronal direction of the cabinet when the individual drawer pan installs normally within the cabinet;

wherein the boundary formed by each of the one or more coronal dividers forms a vertical containment boundary of one or more containment sections selected from the plurality of containment sections contained in the individual drawer pan;

wherein each of the one or more coronal dividers further comprises a sixth set of alignment slots selected from the plurality of alignment slots;

wherein each of the one or more coronal dividers installs into a first alignment slot selected from the plurality of alignment slots while simultaneously inserting into a second alignment slot selected from the plurality of alignment slots;

wherein the plurality of enclosing plates is a disk-shaped plate structure;

wherein the plurality of enclosing plates forms a boundary within the individual drawer pan;

wherein the boundary formed by each of the plurality of enclosing plates forms a vertical containment boundary of one or more containment sections selected from the plurality of containment sections contained in the individual drawer pan;

wherein each of the plurality of enclosing plates installs into a first alignment slot selected from the plurality of alignment slots while simultaneously inserting into a second alignment slot selected from the plurality of alignment slots.

19. The drawer organization system according to claim 18 wherein further subsets of alignment slots selected from the plurality of alignment slots comprises a first set of alignment slots, a second set of alignment slots, a third set of alignment slots, and a fourth set of alignment slots;

wherein the first set of alignment slots is a subset of alignment slots selected from the plurality of alignment slots formed in the interior face of the first pan lateral face;

wherein the second set of alignment slots is a subset of alignment slots selected from the plurality of alignment slots formed in the interior face of the second pan lateral face;

wherein the third set of alignment slots is a subset of alignment slots selected from the plurality of alignment slots formed in the interior face of the third pan lateral face;

wherein each of the third set of alignment slots aligns in the coronal direction with an alignment slot selected from the first set of alignment slots;

wherein the fourth set of alignment slots is a subset of alignment slots selected from the plurality of alignment slots formed in the interior face of the fourth pan lateral face;

wherein each of the fourth set of alignment slots aligns in the coronal direction with an alignment slot selected from the second set of alignment slots.

* * * * *